United States Patent [19]
Cai et al.

[11] Patent Number: 6,051,717
[45] Date of Patent: Apr. 18, 2000

[54] CONVERGENT PROCESS FOR THE PREPARATION OF A MORPHOLINE COMPOUND

[75] Inventors: Dongwei Cai, Edison; Michel Journet, Somerset; Jason Kowal, Iselin; Robert D. Larson, Bridgewater, all of N.J.

[73] Assignee: Merck & Co., Inc., Rahway, N.J.

[21] Appl. No.: 09/428,783

[22] Filed: Oct. 28, 1999

Related U.S. Application Data

[60] Provisional application No. 60/106,291, Oct. 30, 1998.

[51] Int. Cl.[7] .................. C07D 413/06; C07D 249/04
[52] U.S. Cl. ................................ 548/255; 544/132
[58] Field of Search ............................. 548/255; 544/132

[56] References Cited

U.S. PATENT DOCUMENTS 5,612,337  3/1997  Baker et al. ..................... 544/132 X

*Primary Examiner*—Fiona T. Powers
*Attorney, Agent, or Firm*—J. Eric Thies; David L. Rose

[57] ABSTRACT

The present invention is directed to the compound 4-N,N-dimethylaminomethyl-5-formyl-1,2,3-triazole which is a valuable intermediate in the preparation of phamaceutical compounds. The present invention is further directed to a novel convergent process for the preparation of 2-(R)-(1-(R)-(3,5-bis(trifluoromethyl)phenyl)-ethoxy)-4-(5-(dimethylamino)methyl-1,2,3-triazol-4-yl)methyl-3-(S)-(4-fluorophenyl)-morpholine which is a potent and selective substance P (or neurokinin-1) receptor antagonist useful as a therapeutic agent.

18 Claims, No Drawings

CONVERGENT PROCESS FOR THE PREPARATION OF A MORPHOLINE COMPOUND

BACKGROUND OF THE INVENTION

This application claims priority from U.S. Ser. No. 60/106,291, filed Oct. 30, 1998.

The present invention is directed to the compound 4-N,N-dimethyl-aminomethyl-5-formyl-1,2,3-triazole which is a valuable intermediate in the preparation of phamaceutical compounds. The present invention further relates to processes for the preparation of 2-(R)-(1-(R)-(3,5-bis(trifluoromethyl)phenyl)ethoxy)-4-(5-(dimethyl-amino) methyl-1,2,3-triazol-4-yl)methyl-3-(S)-(4-fluorophenyl)-morpholine which is useful as a therapeutic agent, in particular as a potent and selective substance P (or neurokinin-1) receptor antagonist. Substance P antagonists have potential for use in the treatment of inflammatory diseases, emesis, depression, anxiety, and other neuropsychiatric diseases, including bipolar disorder and schizophrenia.

U.S. Pat. No. 5,612,337 describes the preparation of 2-(R)-(1-(R)-(3,5-bis(trifluoromethyl)phenyl)-ethoxy)-4-(5-(dimethylamino)-methyl-1,2,3-triazol-4-yl)methyl-3-(S)-(4-fluorophenyl)morpholine which has the structure:

by a four step process starting from 2-(R)-(1-(R)-(3,5-bis(trifluoromethyl)-phenyl)-ethoxy)-3-(S)-(4-fluorophenyl) morpholine. With reference to Example 12, Method A, of U.S. Pat. No. 5,612,337, the compound is prepared as follows:

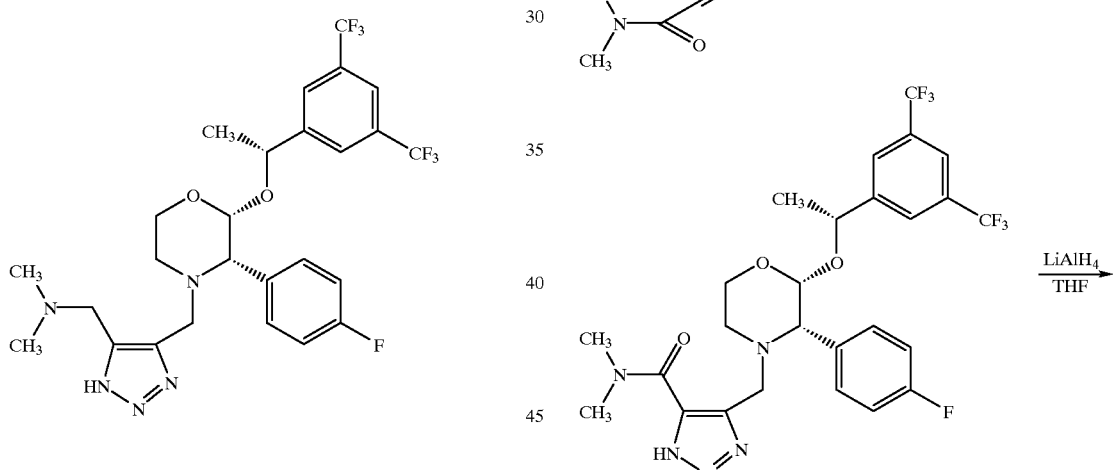

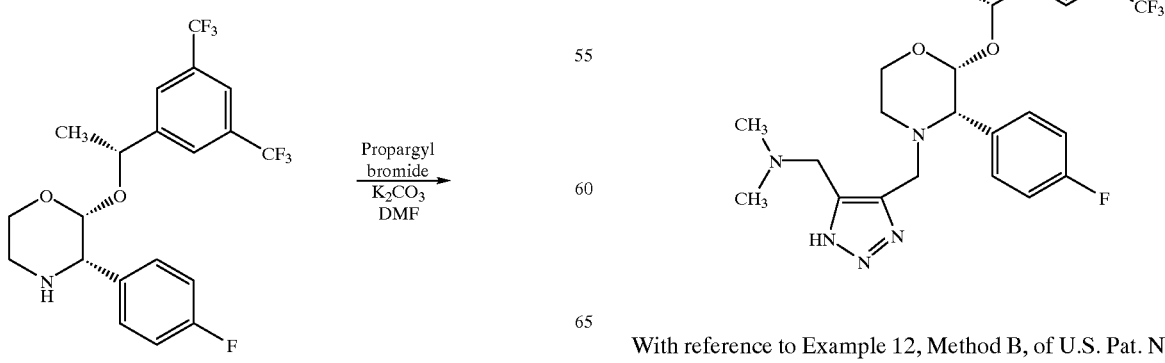

With reference to Example 12, Method B, of U.S. Pat. No. 5,612,337, the compound is also prepared as follows:

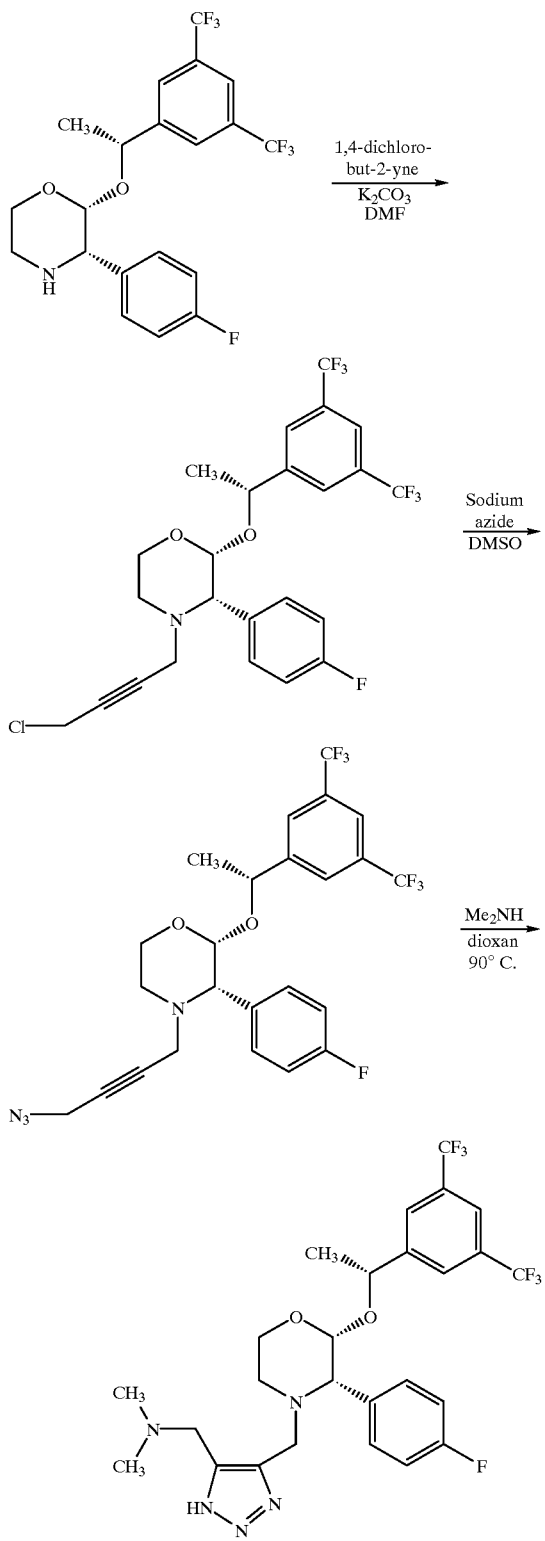

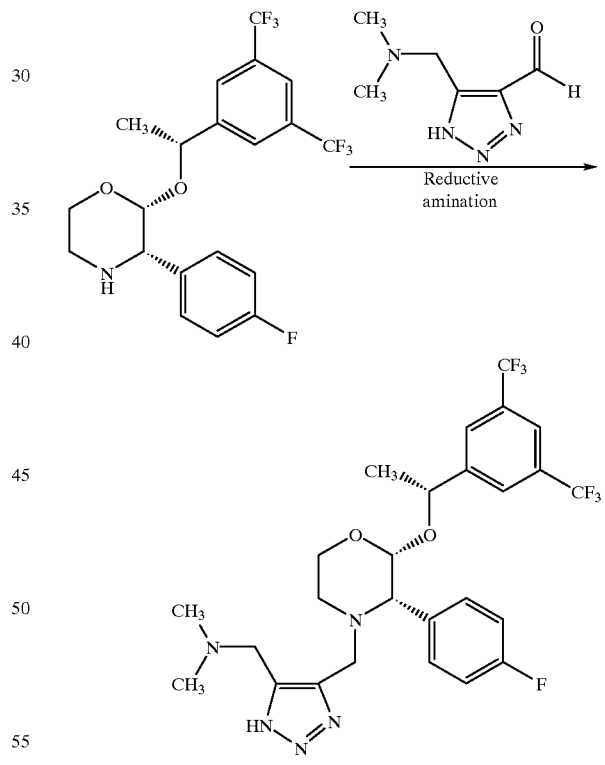

These prior art processes render the synthesis of this compound problematic when attempted on anything other than a laboratory scale. Therefore, there is a need for the development of a process which is readily amenable to scale-up and capable of practical application to a manufacturing plant.

SUMMARY OF THE INVENTION

The present invention is directed to a novel convergent process for the preparation of 2-(R)-(1-(R)-(3,5-bis (trifluoro-methyl)phenyl)-ethoxy)-4-(5-(dimethylamino) methyl-1,2,3-triazol-4-yl)methyl-3-(S)-(4-fluorophenyl) morpholine. This compound is a substance P (neurokinin-l) receptor antagonists which is useful in e.g., inflammatory diseases, emesis, depression, anxiety, and other neuropsychiatric diseases, including bipolar disorder and schizophrenia. In an alternate embodiment, the present invention is directed to the compound 4-N,N-dimethylaminomethyl-5-formyl-1,2,3-triazole which is a valuable intermediate for the preparation of 2-(R)-(1-(R)-(3,5-bis(trifluoro-methyl) phenyl)-ethoxy)-4-(5-(dimethylamino)methyl-1,2,3-triazol-4-yl)methyl-3-(S)-(4-fluorophenyl)morpholine.

DETAILED DESCRIPTION OF THE INVENTION

The present invention is directed to convergent processes for the preparation of 2-(R)-(1-(R)-(3,5-bis(trifluoromethyl) phenyl)-ethoxy)-4-(5-(dimethylamino)methyl-1,2,3-triazol-4-yl)methyl-3-(S)-(4-fluorophenyl)-morpholine.

The general process for the preparation of 2-(R)-(1-(R)-(3,5-bis(trifluoromethyl)phenyl)-ethoxy)-4-(5-(dimethylamino)methyl-1,2,3-triazol-4-yl)methyl-3-(S)-(4-fluorophenyl)morpholine is as follows:

The present invention accordingly provides a convenient, efficient process which utilizes a one-step reductive amination with 4-N,N-dimethylaminomethyl-5-formyl-1,2,3-triazole that conveniently produces 2-(R)-(1-(R)-(3,5-bis (trifluoromethyl)phenyl)-ethoxy)-4-(5-(dimethylamino)-methyl-1,2,3-triazol-4-yl)methyl-3-(S)-(4-fluorophenyl)-morpholine and avoids the need for multiple steps or high temperature cyclization.

Thus, in a first aspect of the present invention there is provided a process for the preparation of 2-(R)-(1-(R)-(3,5- bis(trifluoro-methyl)phenyl)-ethoxy)-4-(5-(dimethylamino) methyl-1,2,3-triazol-4-yl)methyl-3-(S)-(4-fluorophenyl)-morpholine which comprises:

contacting 2-(R)-(1-(R)-(3,5-bis(trifluoromethyl)phenyl)-ethoxy)-3-(S)-(4-fluorophenyl)morpholine with 4-N,N-dimethylamino-methyl-5-formyl-1,2,3-triazole in an organic solvent in the presence of a reducing agent;

to give 2-(R)-(1-(R)-(3,5-bis(trifluoromethyl)phenyl) ethoxy)-4-(5-(dimethylamino)methyl-1,2,3-triazol-4-yl)methyl-3-(S)-(4-fluorophenyl)morpholine.

Suitable reducing agents of use in the above reaction include: sodium triacetoxyborohydride; borane-triethylamine complex; borane-trimethylamine complex; sodium borohydride; sodium cyanoborohydride; borane in the presence of an amine base such as triethylamine; borane-t-butylamine complex; borane-N,N-diethylamine complex; borane-N,N-diisopropylethylamine complex; borane-dimethylamine complex; borane-methylsulfide complex; borane-morpholine complex; borane-pyridine complex; borane-tetrahydrofuran complex; lithium aluminum hydride; lithium borohydride; lithium triethoxy-aluminum hydride; lithium trimethoxyaluminum hydride; catalytic hydrogenation in the presence of metal or organometalic catalysis; and the like. Preferred reducing agents include: sodium triacetoxyborohydride; borane-triethylamine complex; and borane-trimethylamine complex.

Suitable organic solvents of use in the above reaction include an organic solvent selected from the group consisting of: toluene; dimethylformamide; dimethylacetamide; xylene (including o-xylene, m-xylene, p-xylene, and mixtures thereof); benzene; petroleum ether; hexane; heptane; cumene; mesitylene; diethyl ether; tetrahydrofuran; digylme (2-methoxy-ethyl ether); methyl-t-butyl ether; a chlorinated hydrocarbon such as dichloromethane, chloroform, carbon tetrachloride, dichloroethane, chlorobenzene, ortho-dichlorobenzene; and the like; and mixtures thereof. In a preferred embodiment, the organic solvent comprises a solvent which is selected from toluene, dimethylformamide, and mixtures therof. In a more preferred embodiment, the organic solvent comprises a solvent which is selected from dimethylformamide and dimethylacetamide. Other ingredients may be present in the reaction mixture, for example, to facilite the preparation of the product or to monitor the progress of the reaction.

Most preferably, the above reaction is effected in an organic solvent which comprises dimethylacetamide in the presence of sodium triacetoxyborohydride.

A suitable temperature for this reaction is in the range of about 0–100° C., preferably about 20–40° C., and most preferably at room temperature.

Preferably the 2-(R)-(1-(R)-(3,5-bis(trifluoromethyl) phenyl)-ethoxy)-3-(S)-(4-fluorophenyl)morpholine of use in the above reaction is in the form of its toluenesulfonate salt.

In an alternate embodiment, the present invention is directed to the compound 4-N,N-dimethylaminomethyl-5-formyl-1,2,3-triazole which has the following structure:

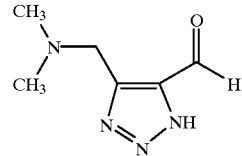

or a salt thereof. Preferred salts of 4-N,N-dimethylaminomethyl-5-formyl-1,2,3-triazole are acid addition salts, such as the salts derived from using inorganic and organic acids. Examples of such acids are hydrochloric, nitric, sulfuric, phosphoric, formic, acetic, trifluoroacetic, propionic, maleic, succinic, malonic and the like. A preferred salt form of 4-N,N-dimethylaminomethyl-5-formyl-1,2,3-triazole is the trifluoroacetic acid salt.

This compound is a valuable intermediate for the preparation of 2-(R)-(1-(R)-(3,5-bis(trifluoro-methyl)phenyl)-ethoxy)-4-(5-(dimethyl-amino)methyl-1,2,3-triazol-4-yl) methyl-3-(S)-(4-fluorophenyl)morpholine.

According to a further aspect of the present invention, there is provided a process for the preparation of 4-N,N-dimethylaminomethyl-5-formyl-1,2,3-triazole which comprises:

(a) treatment of 1-dimethylamino-2-propyne with a strong base to form an acetylide;

(b) treatment of the acetylide with N-methylformanilide;

(c) addition of strong acid to form an acetylinic aldehyde;

(d) treatment of the acetylinic aldehyde with sodium azide to give 4-N,N-dimethylaminomethyl-5-formyl-1,2,3-triazole.

In step (a) above, the strong base is, for example, an organomagnesium halide such as ethylmagnesium chloride, ethylmagnesium bromide or methylmagnesium chloride, or an organolitium reagent such as n-butyllithium, sec-butyllithium, t-butyllithium, and preferably n-butyllithium. Suitable organic solvents of use in step (a) include an organic solvent selected from the group consisting of: diethyl ether; tetrahydrofuran; digylme (2-methoxy-ethyl ether); methyl-t-butyl ether; toluene; dimethylformamide; xylene (including o-xylene, m-xylene, p-xylene, and mixtures thereof); benzene; petroleum ether; hexane; heptane; cumene; mesitylene; and the like; and mixtures thereof. In a preferred embodiment, the organic solvent comprises tetrahydrofuran. A suitable temperature for step (a) is in the range of about –80 to 20° C., preferably about –40 to 0° C., and most preferably about –25 to –15° C.

In step (b) above, the N-methylformanilide is preferably added directly to the reaction mixture and preferably the temperature of the reaction is maintained at about –40 to 0° C. and then the reaction mixture is allowed to warm to room temperature.

In step (c) above, appropriate strong acids include: trifluoroacetic acid; methanesulfonic acid; hydrochloric acid; hydrogen chloride gas; hydrogen bromide; hydrogen iodide; trifluoromethane-sulfonic acid; camphorsulfonic acid; sulfuric acid; phosphoric acid; and an arylsulfonic acid, such as benzenesulfonic acid, p-toluenesulfonic acid, and p-chlorobenzenesulfonic acid. Preferred strong acids include: trifluoroacetic acid; methanesulfonic acid; camphorsulfonic acid; benzenesulfonic acid, p-toluenesulfonic acid; and p-chlorobenzenesulfonic acid. The most preferred strong acid is trifluoracetic acid. In step (c) the temperature of the reaction mixture is preferably kept below about –30.

In step (d) above, the reaction mixture is preferably added to a solution of sodium azide in a solvent such as dimethylformamide, dimethylsulfoxide, dimethoxyethane or dioxane, which may further comprise water.

The preparation of the desired compound with the process of the present invention may be carried out in sequential or convergent synthetic routes. It is noted that in some cases the order of carrying out the subject reactions may be varied to facilitate the reaction or to avoid unwanted reaction products. In general, the process of the present invention is conducted in a convergent manner as presented herein.

NMR spectra were run in $CDCl_3$ and the $^1H$ and $^{13}C$ spectra were measured at 250 and 62.9 MHz. The proton spectra were run with a 10s delay between pulses for the wt % assay. Toluene was dried to less than 150 μg/mL water (by Karl Fisher titration) with 3 Å sieves. Standard inert atmosphere techniques were used for the reaction and work-up.

Many of the starting materials are either commercially available or known in the literature and others can be prepared following literature methods described for analogous compounds. The skills required in carrying out the reaction and purification of the resulting reaction products are known to those in the art. Purification procedures include crystallization, normal phase or reverse phase chromatography.

The following examples are provided for the purpose of further illustration only and are not intended to be limitations on the disclosed invention.

EXAMPLE 1

4-N,N-Dimethylaminomethyl-5-formyl-1,2,3-triazole

| Materials | Amount | Mol (equiv) | MW |
|---|---|---|---|
| 1-Dimethylamino-2-propyne | 16.65 g (12.85 mL) | 0.20 mol | 83.13 |
| n-Butyllithium (1.6 M in hexanes) | 125 mL | 0.20 mol | |
| N-Methylformanilide | 27.05 g or 24.7 mL | 0.20 mol | 135.17 |
| Trifluoroacetic acid | 22.80 g or 15.4 mL | 0.20 mol | 114.02 |
| Sodium azide | 12.35 g | 0.19 mol | 65.01 |
| THF | 200 mL | | |
| DMF | 500 mL | | |
| Water | 25 mL and 200 mL | | |
| MTBE | 600 mL | | |

1-Dimethylamino-2-propyne (16.65 g, 12.85 mL, 0.2 mol) was dissolved in THF (200 mL) and the resulting yellow homogeneous solution was cooled in a dry ice-acetone bath. n-Butyllithium (1.6M in hexanes, 125 mL, 0.2 mol) was added over ca. 5 minutes maintaining the temperature at −25 to −15° C. n-Butyllithium was titrated with N-pivaloyl-o-toluidine (J. Org. Chem. 1989, 54, 509.). After completion of the addition, the reaction mixture was white pasty (but stirrable) due to the aggregates of the acetylide at high concentration.

N-Methylformanilide (27.05 g, 24.7 mL, 0.2 mol) was added in one portion and the reaction mixture was allowed to warm to room temperature over ca. 15 minutes and further aged at this temperature for 30 minutes. The addition of N-Methylformanilide wasn't exothermic at −20° C. The reaction becomes clear homogeneous (slightly yellow) at around 0° C.

The reaction mixture was then cooled over a dry ice-acetone bath and trifluoroacetic acid TFA (22.80 g, 15.4 mL, 0.2 mol) was added over ca. 10 minutes maintaining the temperature below −30° C. The resulting acetylenic aldehyde was not stable for more than 1–2 hours at −30° C. (more stable at lower temperature). The reaction mixture was yellow and would turn to dark brown upon decomposition of the aldehyde. Crude acetylenic aldehyde must be quenched into sodium azide within 1 to 2 hours.

The reaction mixture (kept below −30° C.) was then added to a DMF solution (500 mL) containing sodium azide (12.35 g, 0.19 mol) and water (25 mL) at room temperature over ca. 15 minutes. Final temperature of the batch was ~18° C. The solution was orange-red with a pH$\geq$1 2. At this stage, the solution is stable for several days at room temperature.

The reaction mixture was diluted with water (200 mL) and extracted with MTBE (3×200 mL). The aqueous solution (2.5/1 DMF/water) was pH adjusted to 8.5 with aqueous HCl (12N, ca. 10 mL). Assay yield was 95% (based on limiting reagent sodium azide, 27.7 g assay of heterocycle, 0.18 mol). N-methylaniline byproduct and non-reacted N-methylformanilide are extracted in the MTBE layer. The heterocycle remains into the aqueous along with inorganic salts and was >98 A % (at 260 nm).

The product was isolated by first using about 6 eq. of strong acidic ion exchange resin (eq. Dowax or AG-50), then washed with several volume of water then the product was eluted with IPA/water/NH$_3$. The resulting aqueous layer was concentrated to remove water and product was crystallized in IPA. The product 4-N,N-dimethylaminomethyl-5-formyl-1,2,3-triazole was a highly crystalline compound and it has low solibility in dry IPA (4 mg/mL in IPA with KF less than 400 μg/mL). The product can be filtered and dried and it was stable at room temperature under air. 4-N,N-Dimethylaminomethyl-5-formyl-1,2,3-triazole: $C_6H_{10}N_4O$, Mol. Wt.: 154.17

$^1$H NMR (, 250 MHz, D$_3$O; all peaks are singlets): Free Base: 9.95 ppm (1 H), 4.4 ppm (2 H), 2.80 ppm (6 H). TFA Salt: 10.1 ppm (1 H), 4.5 ppm (6 H), 2.88 ppm (2 H).

Analytical conditions:

Metachem inertsil ODS-3 (250×4.6); 1.0 mL/min.; detection at 220 and 260 nm; HP 1100; A: H$_2$O (buffered to pH 7); B: Acetonitrile. −99% A at 0.0 min; 90% A at 10.0 min; 30% A at 20.0 min. NaN$_3$: 2.85 min (does not abosb @260 nm) 4-N,N-dimethylaminomethyl-5-formyl-1,2,3-triazole: 6.75 min DMF: 7.85 min (does not abosb @260 nm) N-methylformanilide: 19.85 min N-methylaniline: 22.55 min

EXAMPLE 2

4-N,N-Dimethylaminomethyl-5-formyl-1,2,3-triazole

| Materials | Amount | Mol (equiv) | MW |
|---|---|---|---|
| 1-Dimethylamino-2-propyne | 16.65 g | 0.20 mol | 83.13 |
| EtMgCl (2.0 M in THF) | 110.0 mL | 0.22 mol | |
| N-Methylformanilide | 32.4 g (29.6 mL) | 0.24 mol | 135.17 |
| Sodium azide | 12.35 g | 0.19 mol | 65.01 |
| THF | 90 mL | | |
| DMSO | 400 mL | | |
| Water | 20 mL | | |
| Aqueous 1.0 M HCl | ca. 200 mL | ca. 0.4 mol | |
| Ethyl acetate | 200 mL | | |
| Dowex ® 50W X8-100 | 590 mL | | |
| Water | 1.8 L | | |
| Acetonitrile/water/triethylamine(6:3:1) | 1.8 L | | |
| Isopropyl alcohol | 1240 mL | | |

1-Dimethylamino-2-propyne (16.65 g, 21.54 mL, 0.2 mol) was dissolved in THF (90 mL) and EtMgCl (2.0M in THF, 110.0 mL, 0.22 mol) was added to the resulting yellow homogeneous solution over 10–15 minutes maintaining the temperature at 20–25° C. The reaction mixture was aged at this temperature for 2 hours. The addition was slightly exothermic and was controlled by cooling.

N-Methylformanilide (32.4 g, 29.6 mL, 0.24 mol) was added at room temperature over ca. 10 minutes. The reaction mixture was aged for 60 minutes. The addition was exothermic and was controlled by cooling.

In a separate flask sodium azide (12.35 g, 0.19 mol) was dissolved in DMSO (400 mL) and water (20 mL). The solution was stirred vigorously while the magnesium acetylide mixture was added at 20–25° C. over 15–30 minutes. The reaction was exothermic and was controlled by cooling. The final temperature of the reaction mixture was ~20° C. The solution was yellowish and hazy due to the magnesium salts. The solution was stable for several days at room temperature.

The reaction mixture was pH adjusted with aqueous hydrochloric acid (1.0M) to pH 7.0–7.5 and diluted with ethyl acetate (200 mL). The layers are separated. The assay yield of 1-dimethylamino-2-propyne was 90% based on the acetylene and 95% based on sodium azide (27.75 g assay of heterocycle, 0.18 mol). About 90% of N-methylaniline byproduct and non-reacted N-methylformanilide are extracted in the ethyl acetate layer.

The aqueous solution was loaded onto the ion exchange resin column (strongly acidic resin Dowex® 50 W X8-100; 1.7 meq/mL wet, 5 equiv, 1.0 mol, 590 mL) at a flow rate of 4–5 bed volumes per hour. The Dowex® 50 W X8-100 must be properly regenerated prior to use. The resin was then washed with three bed volumes of deionized water (1.8 L) at a flow rate of 4–5 bed volumes per hour to remove the DMSO. The wash solution on the resin was displaced with one bed volume of a mixture of acetonitrile/water/triethylamine (6:3:1). The flow was stopped and the column was aged for 16 hours.

At this stage, the heterocycle was still on the resin. The aging allows equilibration reducing the volume of base wash. The first bed volume was collected and two additional bed volumes are eluted over ca. one hour providing a 95% assay recovery of the heterocycle (26.4 assay g, 0.171 mol). The combined fractions are concentrated to 100 mL. Isopropyl alcohol (600 mL) was added and the mixture was concentrated to 100 mL. This procedure was repeated until the level of water and triethylamine are reduced to <1 V %. The product crystallizes during the solvent switch. The volume was adjusted to ~250 mL. The triazole aldehyde was filtered, washed with isopropyl alcohol (~40 mL) and dried at 40° C. under vacuum with a nitrogen stream affording 25 g of pure compound (>99 wt %) in an overall 80% isolated yield (based on 1-dimethylamino-2-propyne).

Analytical conditions:

Metachem inertsil ODS-3 (250×4.6); 0.75 mL/min.; detection at 200, 220 and 240 nm; HP 1100; A: $H_2O$ (buffered to pH 7); B: Acetonitrile. –99% A at 0.0 min; 70% A at 20.0 min; 30% A at 25.0 min; 0% A at 30.0 min. 4-N,N-dimethylaminomethyl-5-formyl-1,2,3-triazole: 2.85 min N-methylaniline: 4.55 min (strong (200 nm; weak @220 and 240 nm) $NaN_3$: 7.5 min (strong @200 nm) Ethyl acetate: 18.60 min N-methylformanilide: 25.65 min

EXAMPLE 3

4-N,N-Dimethylaminomethyl-5-formyl-1,2,3-triazole

| Materials | Amount | Mol (equiv) | MW |
|---|---|---|---|
| 1-Dimethylamino-2-propyne | 16.65 g | 0.20 mol | 83.13 |
| EtMgCl (2.0 M in THF) | 110.0 mL | 0.22 mol | |
| N-Methylformanilide | 32.4 g (29.6 mL) | 0.24 mol | 135.17 |
| Sodium azide | 12.35 g | 0.19 mol | 65.01 |
| THF | 90 mL | | |
| DMSO | 400 mL | | |
| Water | 20 mL | | |

-continued

4-N,N-Dimethylaminomethyl-5-formyl-1,2,3-triazole

| Materials | Amount | Mol (equiv) | MW |
|---|---|---|---|
| Aqueous 1.0 M HCl | ca. 420 mL | ca. 0.42 mol | |
| Ethyl acetate | 200 mL | | |
| Dowex ® 50 W X8-100 | 600 mL | | |
| Water | 1.2 L | | |
| Acetonitrile/water/triethylamine (6:3:1) | 1.8 L | | |
| 2-Butanol | 640 mL | | |

1-Dimethylamino-2-propyne (16.65 g, 21.54 mL, 0.2 mol) was dissolved in THF (90 mL). EtMgCl (2.0M, 110.0 mL, 0.22 mol) was added to the yellow homogeneous solution over 10–15 minutes maintaining the temperature at 20–25° C. The reaction mixture was aged for 2 hours. N-Methylformanilide (27.05 g, 24.7 mL, 0.24 mol) was added at room temperature over ca. 10 minutes and the mixture was aged for 60 minutes. The additions of EtMgCl and N-Methylformanilide are slightly exothermic and are controlled by cooling.

The solution of the magnesium acetylide was added to a vigorously stirred solution of sodium azide (12.35 g, 0.19 mol) in DMSO (400 mL) and water (20 mL) at 20–25° C. over 15–30 minutes. The reaction was exothermic and was controlled by cooling. The reaction mixture was yellow and hazy (magnesium salts). The product in the reaction mixture was stable for several days at room temperature.

The reaction mixture was pH adjusted with aqueous HCl (1.0M) until pH 7.0 to 7.5. The solution was washed with ethyl acetate (200 mL). About 90% of N-methylaniline byproduct and unreacted N-methylformanilide are extracted into the ethyl acetate. The assay yield was 90% based on 1-dimethylamino-2-propyne and 95% based on sodium azide (27.75 g assay of heterocycle, 0.18 mol). No azide was detected by assay (LOD<50 ppm).

The crude reaction mixture was loaded onto the strongly acidic resin Dowex® 50 W X8-100 (1.7 meq/mL wet, 5 equiv, 600 mL) at a flow rate of 4–5 bed volumes per hour.

The Dowex® 50 W X8 must be properly generated prior to use. For fresh resin the bed was washed with 1.5 bed volumes of 90% methanol/water to remove any monomer and other organic soluble impurities. The procedure for 1 L of resin follows: Slurry one liter of Dowex® 50W resin in water, transfer into a suitable column and drain the water to the top of the bed. The bed was washed with 90% methanol/water (1.5 L) at a flow rate of 25 minutes per bed volume (1 L). One bed volume of water (1 L) was used to rinse the column. A 1N NaOH solution (3 L) was passed through the column, followed by 1 bed volume of water (1 L) as a rinse. The column was returned to the acid cycle with one bed volume of 1N HCl (3 L). A final rinse with one bed volume of water and the resin column was ready for use. The column was regenerated as follows: The column was washed with one bed volume of water, and then 3 bed volumes of 1N HCl. A final water wash with one bed volume of water readies the column for reuse. The resin was then washed with 2 bed volumes of deionized water (1.2 L) at a flow rate of 4–5 bed volumes per hour to remove DMSO.

The product was then eluted with a mixture of acetonitrile:water:triethylamine (6:3:1). After 1 bed volume (~600 mL) was added to the column displacing the water wash, the flow was stopped and the column was equilibrated for 1–2 h. Any breakthrough during the solvent switch can be recycled back to the column. At this stage, the product was on the resin. The age allows equilibration reducing the volume of base wash. An additional 1.5 bed volumes (1.2 L) are eluted over ~1 h providing 97% assay recovery of the heterocycle (26.4 assay g, 0.171 mol). The total elution volume was 2.5 bed volumes. Only 1.5 bed volumes are collected leaving one bed volume on the column. A total of 1.5 bed volumes are collected (~900 mL). The rich cuts are concentrated to ~100 mL. 2-Butanol (300 mL) was added and the mixture was concentrated again to 100 mL. 2-Butanol (300 mL) was added and the concentration was repeated until water and triethylamine are reduced to <1% each. During the second concentration, the product crystallized. The final volume was adjusted to 150 mL. The crystalline product was filtered, washed with 2-butanol (~40 mL) and dried at 40° C. under vacuum with a nitrogen stream to afford 25 g of pure triazole aldehyde (>99 wt %) in 80% overall isolated yield based on 1-dimethylamino-2-propyne.

EXAMPLE 4

4-N,N-Dimethylaminomethyl-5-formyl-1,2,3-triazole

| Materials | Amount | Mol (equiv) | MW |
|---|---|---|---|
| 1-Dimethylamino-2-propyne | 457.0 g (593.0 mL) | 5.50 mol | 83.13 |
| EtMgCl (2.0 M in THF) | 3.02 L | 6.05 mol | |
| N-Methylformanilide | 892 g (813 mL) | 6.60 mol | 135.17 |
| Sodium azide | 339.7 g | 5.22 mol | 65.01 |
| THF | 2.5 L + 0.4 L | | |
| DMSO | 11.0 L | | |
| Water | 330.0 mL | | |

A 12-L flask fitted with a mechanical stirrer, thermocouple, nitrogen inlet and 5-L addition funnel was charged with 1-dimethylamino-2-propyne (457 g as is, 593 mL, 5.50 mol) and dry tetrahydrofuran (2.5 L). The resulting yellow homogeneous solution was cooled to ~10° C. and EtMgCl (2.0M, 3.02 L, 6.05 mol) was added over 30 min while maintaining the temperature at 20–25° C. The reaction mixture was aged at ambient temperature for 2 h. N-Methylformanilide (892 g, 813 mL, 6.60 mol) was then added over 20 min while maintaining the reaction temperature at 20–25° C. The resulting clear yellow-to-green mixture was aged at room temperature for 1 h. The additions of EtMgCl and N-methylformanilide are slightly exothermic. The temperature was controlled by cooling the reaction mixture. During the Grignard addition, ethane was produced (ca. 125 L).

The reaction mixture was transferred into a vigorously stirred DMSO solution (11.0 L) containing sodium azide (339.7 g, 5.22 mol) and water (330 mL, 18.3 mol) over 30 min while maintaining the temperature between 15° C. and 25° C. The 12-L flask was rinsed with THF (0.4 L). The reaction was exothermic and was controlled by cooling the reaction mixture. A 50 L flask was used since the final volume after dilution with toluene and Aliquat® was 40 L. Assay yield (763 g assay of heterocycle, 4.95 mol) was ~90% based on 1-dimethylamino-2-propyne and ~95% based on sodium azide. The level of residual sodium azide was assayed at <30 ppm. The reaction mixture was yellow-orange and hazy due to magnesium salts. The pH of the mixture was 9.7.

EXAMPLE 4A

4-N,N-Dimethylaminomethyl-5-formyl-1,2,3-triazole: Extractive Isolation Process

| Materials | Amount | Mol (equiv) | MW |
|---|---|---|---|
| Water | 18 L | | |
| Toluene | 33 L | | |
| Aliquat ® 336 | 6.67 Kg (7.5 L) | 16.50 mol | 404.17<br>d = 0.884 |
| Glacial acetic acid | 630 mL | 11.0 mol | 60.05<br>d = 1.049 |
| 2-Butanol | ca. 13 L | | |

To the reaction mixture from Example 4 was added Aliquat® 336 (4.44 kg, 5.0 L, 11.0 mol) and toluene (11.0 L). The mixture was stirred under nitrogen for 30 min and transferred into an extractor. Water (6.0 L) was added affording two phases. The layers are well-mixed and separated. The aqueous layer was back-extracted with a solution of Aliquat® 336 (1.11 kg, 2.75 mol) in toluene (11.0 L). The layers are separated and the aqueous layer was back-extracted once again with Aliquat® 336 (1.11 kg, 2.75 mol) in toluene (11.0 L).

The final aqueous layer was slightly gelatinous due to the suspended magnesium salts. The pH was 9.7. At this stage 94% of the product (~715 assay g of triazole aldehyde, 4.65 mol) has been extracted into the combined organic layers. The combined organic layers also contain 35 A % of DMSO, as compared to the triazole aldehyde, Aliquat® 336, the N-methylaniline byproduct and excess of N-methylformanilide.

The combined organic layers are washed with water (6.0 L) to remove the DMSO. Less than 1% of triazole aldehyde was extracted into the aqueous layer (ca. 0.6%). The organic layer contains ca. 3 A % of DMSO. The resulting combined organic layer was washed with water (4.5 L) containing glacial acetic acid (630 mL, 11.0 mol) to release the triazole aldehyde. The layers are separated and the organic layer was washed once again with water (2.0 L).

The two extractions recover 95% of the triazole aldehyde (85% in first one and 10% in second one). The N-methylaniline byproduct and the excess N-methylformanilide remain in the organic layer. At this stage an 86% overall recovery (~660 assay g, 4.25 mol) of the triazole aldehyde has been achieved.

The combined aqueous layers are concentrated to 1.5 L. 2-Butanol (12 L) was added and the mixture was concentrated to ~2 L. This procedure was repeated until the level of water was reduced to <0.5 V %. The product crystallizes during the solvent switch.

The volume was adjusted to ~3 L. The triazole aldehyde was filtered, washed with 2-butanol (1.0 L) and dried at 40° C. under vacuum for 16 h with a nitrogen stream affording 562 g of pure triazole aldehyde (>99.5 A %, >98.5 wt %) as an off-white shiny crystalline solid. The overall isolated yield was 66% based on 1-dimethylamino-2-propyne. The loss to the mother liquors (98 assay g) was 15%.

EXAMPLE 4B

| 4-N,N-Dimethylaminomethyl-5-formyl-1,2,3-triazole: Salt Filtration Isolation Process | | | |
|---|---|---|---|
| Materials | Amount | Mol (equiv) | MW |
| Water | 18.5 L | | |
| Toluene | 14.5 L | | |
| Aliquat ® 336 | 6.67 kg (7.5 L) | 16.50 mol | 404.17 d = 0.884 |
| Solka-floc | 3000 mL | | |
| Glacial acetic acid | 630 mL | 11.0 mol | 60.05 d = 1.049 |
| 2-Butanol | ca. 13 L | | |

The same mixture of the sodium salt of the triazole aldehyde in DMSO/THF from Example 4 was alternatively treated as follows: To the reaction mixture was added Aliquat® 336 (6.67 kg, 7.5 L, 16.5 mol) and toluene (11.0 L). The mixture was yellow-orange in color and hazy due to magnesium salts. This mixture was aged under nitrogen for 2 h. The salts are removed by filtration through a pad of solka-floc (3000 mL; ~3 inches in a 6-L sintered-glass funnel). The filtration removes the sodium chloride formed by the displacement of the Aliquot chloride with the sodium salt of the triazole. This leaves the Aliquot as a soluble salt of the triazole in toluene. Filtration of the mixture takes ~1.5 h. About 1.5 inches of salts relative to the 3 inches of the solka-floc cake are removed.

The pad of solka-floc was rinsed with toluene (3.5 L). The resulting hazy-yellow filtrate was transferred into an extractor and diluted with water (6.0 L). The mixture separates into two phases. The layers are well-mixed and separated. The resulting aqueous layer was slightly gelatinous due to the magnesium salts. The pH was 9.7. At this stage ~89% of product (~680 assay g, 4.40 mol) has been extracted. The toluene layer contains the triazole aldehyde along with ~35 A % of DMSO (relative to the triazole aldehyde), Aliquat® 336, the N-methylaniline byproduct and excess N-methylformanilide.

The organic layer was washed with water (6.0 L) to remove the DMSO. The toluene layer contains ~3 A % of DMSO. Less than 1% of the triazole aldehyde was lost in the aqueous layer (~0.6%). The organic layer was washed with water (4.5 L) containing glacial acetic acid (630 mL, 11.0 mol) to release the triazole aldehyde. The layers are separated and the organic layer was washed with water (2.0 L). These two extractions recover 94% of the triazole aldehyde (85% in the first and 9% in the second). The N-methylaniline byproduct and excess N-methylformanilide remain in the organic layer. At this stage 81% overall of triazole aldehyde (~620 assay g, 4.0 mol) has been recovered. The combined aqueous layers are concentrated to ~1.5 L. 2-Butanol (12 L) was added and the mixture was concentrated to ~2 L. This procedure was repeated until the level of water was reduced to <0.5 V %. The product crystallizes during the solvent switch.

The volume was adjusted to 3 L. The solid was filtered, washed with 2-butanol (1.0 L) and dried at 40° C. under vacuum with a nitrogen stream for 16 h to afford 520 g of pure triazole aldehyde (>99.5 A %, >98.5 wt %) as an off-white shiny crystalline solid. The overall isolated yield was 61% (based on 1-dimethylamino-2-propyne). The loss to the mother liquors (95 assay g) was 16%.

EXAMPLE 5

| 4-N,N-Dimethylaminomethyl-5-formyl-1,2,3-triazole | | | |
|---|---|---|---|
| Materials | Amount | Mol (equiv) | MW |
| 1-Dimethylamino-2-propyne | 26.2 g | 0.315 mol | 83.13 |
| EtMgCl (2.0 M in THF) | 173 mL | 0.346 mol | |
| N-Methylformanilide | 51.1 g (46.7 mL) | 0.378 mol | 135.17 |
| Sodium azide | 19.5 g | 0.300 mol | 65.01 |
| THF | 70 mL | | |
| DMSO | 500 mL + 90 mL + 60 mL | | |
| Water | 8.1 mL | 0.450 mol | 18.0 |
| Hydrogen chloride HCl (4.2 N/IPA) | 145 mL | 0.610 mol | |
| Piperidine | 29.4 g (34.2 mL) | 0.346 mol | 85.15 |
| Ethyl acetate | 310 mL + 150 mL | | |
| Trifluoroacetic acid (TFA) | 26.7 g (18.0 mL) | ca. 0.234 mol | 114.02 (d: 1.48) |
| Solka-floc | ca. 100 mL | | |

A 500 mL flask fitted with an over-head stirrer, a thermocouple, an inlet of nitrogen and a 250 mL dropping funnel was charged with 1-dimethylamino-2-propyne (26.2 g not corrected for purity, 0.315 mol) and THF (70 mL). The resulting yellow homogeneous solution was cooled over an ice bath to ca. +10° C. and EtMgCl (2.0M, 173 mL, 0.346 mol) was added over 30 minutes maintaining the temperature between +20 and +25° C. After completion of the addition, the reaction mixture was warmed to room temperature (20 to 25° C.) and aged for 2 hours. N-Methylformanilide (51.1 g, 46.7 mL, 0.378 mol) was then added over ca. 20 minutes while maintaining the reaction temperature between +20 and +25° C. The resulting yellow-green (clear homogeneous) mixture was aged at room temperature for 1 hour. The additions of EtMgCl and N-methylformanilide are slightly exothermic. During the Grignard addition, ethane was produced (ca. 7 L).

The reaction mixture was added into a vigorously stirred solution of DMSO (500 mL) containing sodium azide (19.5 g, 0.3 mol) and water (8.1 mL, 0.45 mol) over 30 minutes while maintaining the temperature between +15° C. and +25° C. The reaction was exothermic and was controlled by cooling the reaction mixture. The final temperature of the batch was ca. +20° C. The assay yield was 91% based on 1-dimethylamino-2-propyne and 96% based on sodium azide (44.2 g assay of heterocycle, 0.287 mol). The level of remaining sodium azide was assayed at <30 ppm. The reaction mixture was yellow-orange and hazy and the pH was 9.7.

Hydrogen chloride (4.2N HCl in IPA, 145 mL, 0.61 mol) was added over ca. 15 minutes while maintaining the temperature between +20 and +25° C. After completion of the addition, the resulting yellow-orange slurry of magnesium salts was concentrated to remove THF and IPA. The mixture was filtered through a pad of solka-floc (100 mL; ca. 0.5 inch in a 600 mL sintered glass funnel) to remove the insoluble salts. The pad of solka-floc was rinsed with DMSO (90 mL). The resulting filtrate was clear yellow-orange. The pH was 8.25. The target for the pH was 7.0 to 8.5, measured from an aliquot of the solution diluted with an equal volume of water. Using TFA instead of HCl (4N in IPA) for the neutralization led to a lower recovery of dimer (ca. 70% vs 85%) which was likely due to a poorer removal of inorganic salts.

Piperidine (34.2 mL, 0.346 mol) in ethyl acetate (310 mL) (344 mL, ~1M) was added to the resulting DMSO filtrate over 2–3 hours and the reaction was aged at room temperature for ca. 16 h. The dimer adduct crystallizes during the addition of piperidine to give a stirrable slurry.

The resulting yellow slurry was filtered to afford the dimer adduct as a white solid, which was washed with DMSO (60 mL) and ethyl acetate (150 mL), and dried at 40° C. under vacuum with a nitrogen stream for 16 hours to afford 62.1 g of product (95 A %, ca. 87 wt %) as a white solid. The isolated yield was 74.5% based on 1-dimethylamino-2-propyne and 78% based on sodium azide (54.0 g assay of dimer, 0.117 mol). The filtration was fast. The solubility of the product in the filtrate was ca.10 g/L as triazole-aldehyde equivalent, which represents a yield loss of 18%. The pH of filtrate was 10.3. The dimer was pure. The low wt % (87 wt %) was due to residual DMSO, which does not affect the next step.

The piperidine adduct (62.1 g, 87 wt %, 54.0 g assay, 0.117 mol) was slurried in IPA/water (98:2, 365 mL). TFA (26.7 g, 18.0 mL, 0.234 mol) was added over 10 minutes maintaining the temperature at 20–25° C. The triazole aldehyde was liberated during the pH adjustment. The product crystallized from the reaction mixture.

The slurry was stirred for 2 hours at room temperature. The triazole-aldehyde was filtered, washed with IPA (40 mL) and dried at 40° C. under vacuum with a nitrogen stream for 16 hours to afford 30.5 g of pure product (>99.9 A %, >99.5 wt %) as a white crystalline solid. The isolated yield was 63% based on 1-dimethylamino-2-propyne and 65.5% based on sodium azide.

EXAMPLE 6

2-(R)-(1-(R)-(3,5-bis(trifluoromethyl)phenyl)-ethoxy)-4-(5-(dimethylamino)-methyl-1,2,3-triazol-4-yl)methyl-3-(S)-(4-fluorophenyl)morpholine 2-(R)-(1-(R)-(3,5-bis(trifluoromethyl)phenyl)-ethoxy)-3-(S)-(4-fluorophenyl)morpholine TsOH salt (609 g, 1 mol) and 4-N,N-dimethylaminomethyl-5-formyl-1,2,3-triazole (225 g, 1.5 mol) are suspended in 3L of toluene and 1 L of DMF. The resulting suspension was stirred for 30 minutes, then 1 eq. of sodium triacetoxyborohydride (212 g, 1 mol) was added. After 30 minutes, another portion of sodium triacetoxyborohydride (212g, 1 mol) was added. The resulting solution/suspension was aged at 25° C. for 5 hours and the reaction was completed when starting material secondary amine was less than 0.1 A % (at 220 nm) as judged by LC. When the reaction was completed, 2 eq. of 1N HCl (2 L, 2 mol) was added and the reaction mixture was aged for 4 hours (to break some boron complexes). The solution was then neutralized back to pH=8~9 with NaOH or Na$_3$PO$_4$ and extracted with toluene (3 L) and organic layer was washed twice with water and concentrated to obtain 2-(R)-(1-(R)-(3,5-bis(trifluoro-methyl)phenyl)-ethoxy)-4-(5-(dimethylamino)-methyl-1,2,3-triazol-4-yl)methyl-3-(S)-(4-fluorophenyl)morpholine.

EXAMPLE 7

| 2-(R)-(1-(R)-(3,5-bis(trifluoromethyl)phenyl)-ethoxy)-4-(5-(dimethylamino)-methyl-1,2,3-triazol-4-yl)methyl-3-(S)-(4-fluorophenyl)morpholine | | |
|---|---|---|
| Materials | Amount | MW |
| 2-(R)-(1-(R)-(3,5-bis(trifluoromethyl)-phenyl)ethoxy)-3-(S)-(4-fluorophenyl)-morpholine TsOH salt | 609 g (1 mol) | 609 |
| 4-N,N-dimethylaminomethyl-5-formyl-1,2,3-triazole | 200 g (1.3 mol) | 154.17 |
| NaBH(OAc)$_3$ | 414 g (95 wt %, 1.9 mol) | 211.94 |
| DMAC (Dimethylacetamide) | 2.7 L | |

To 4-N,N-dimethylaminomethyl-5-formyl-1,2,3-triazole (200 g, 1.3 mol) in dimethylacetamide (1.7 L) at 0~–5° C. was charged with 2-(R)-(1-(R)-(3,5-bis(trifluoromethyl)phenyl)ethoxy)-3-(S)-(4-fluorophenyl)morpholine TsOH salt (609 g, 1 mol). The resulting slurry was transferred into another vessel and 0.3 L of dimethylacetamide was used for the rinse. Then a solution of NaBH(OAc)$_3$ (414 g, 1.9 mol) in dimethylacetamide (0.7 L) was added (prepared off line using another vessel). It was necessary to cool down the solution to 0~–5° C. to avoid side reaction during charging with the secondary amine. The reaction was slow at 0 to –5° C. and it was slightly exothermic. The reaction solution was slowly heated up to 40° C. and was maintained for 1 hour to complete the reaction. The reaction was judged completely by HPLC when the secondary amine was less than 0.1 A % (220 nm).

Aqueous HCl (1.33 L, 3N, 4 mol) was then added (maintaining 40° C. with cooling during HCl charge) and aged for 2 hours at 40° C. (to destroy some excess sodium triacetoxyborohydride and to break some boron complexes). Toluene (3 L) was added, then the solution was neutralized back to pH=8~9 with NaOH (5N, ~2 L). It was necessary to add toluene (3 L) before adjusting pH to avoid free base of the product precipitate as a gum ball. Additional water (2.1 L) was added and the organic layer was separated, washed twice with water (4 L) and constant volume distillation to remove the water azeotropically to give a solution of 2-(R)-(1-(R)-(3,5-bis(trifluoromethyl)phenyl)ethoxy)-4-(5-(dimethylamino)methyl-1,2,3-triazol-4-yl)methyl-3-(S)-(4-fluorophenyl)morpholine.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, reaction conditions other than the particular conditions as set forth herein above may be applicable as a consequence of variations in the reagents or methodology to prepare the compounds from the processes of the invention indicated above. Likewise, the specific reactivity of starting materials may vary according to and depending upon the particular substituents present or the conditions of manufacture, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound which is 4-N,N-dimethylaminomethyl-5-formyl-1,2,3-triazole, or a salt thereof.

2. The compound of claim 1 which is 4-N,N-dimethylaminomethyl-5-formyl-1,2,3-triazole trifluoroacetic acid salt.

3. A compound 4-N,N-dimethylaminomethyl-5-formyl-1,2,3-triazole.

4. A process for the preparation of 4-N,N-dimethylaminomethyl-5-formyl-1,2,3-triazole which comprises:
   (a) treatment of 1-dimethylamino-2-propyne with a strong base to form an acetylide;
   (b) treatment of the acetylide with N-methylformanilide;
   (c) addition of strong acid to form a acetylinic aldehyde;
   (d) treatment of the acetylinic aldehyde with sodium azide to give 4-N,N-dimethylaminomethyl-5-formyl-1,2,3-triazole.

5. The process of claim 4 wherein step (a) the strong base is ethylmagnesium chloride or n-butyllithium.

6. The process of claim 4 wherein step (a) the strong base is ethylmagnesium chloride.

7. The process of claim 4 wherein step (b) the N-methylformanilide is added directly to the acetylide.

8. The process of claim 4 wherein step (c) the strong acid is trifluoroacetic acid.

9. The process of claim 4 wherein step (d) the acetylinic aldehyde is added to a solution of sodium azide which comprises a solvent selected from dimethylformamide, dimethylsulfoxide, dimethoxyethane and dioxane, and which may further comprise water.

10. The process of claim 9 wherein step (d) the solvent is dimethylsulfoxide.

11. The process of claim 10 wherein step (d) the solvent further comprises water.

12. A process for the preparation of 2-(R)-(1-(R)-(3,5-bis(trifluoromethyl)phenyl)ethoxy)-4-(5-(dimethyl-amino)methyl-1,2,3-triazol-4-yl)methyl-3-(S)-(4-fluorophenyl)morpholine which comprises:
   contacting 2-(R)-(1-(R)-(3,5-bis(trifluoromethyl)phenyl)-ethoxy)-3-(S)-(4-fluorophenyl)morpholine with 4-N,N-dimethylaminomethyl-5-formyl-1,2,3-triazole in an organic solvent in the presence of a reducing agent;
   to give 2-(R)-(1-(R)-(3,5-bis(trifluoromethyl)phenyl)ethoxy)-4-(5-(dimethyl-amino)methyl-1,2,3-triazol-4-yl)methyl-3-(S)-(4-fluorophenyl)-morpholine.

13. The process of claim 12 wherein the reducing agent is selected from: borane-triethylamine complex; borane-trimethylamine complex; and sodium triacetoxyborohydride.

14. The process of claim 12 wherein the reducing agent is sodium triacetoxyborohydride.

15. The process of claim 12 wherein the organic solvent comprises a solvent which is selected from toluene, dimethylformamide, dimethylacetamide, and mixtures therof.

16. The process of claim 12 wherein the organic solvent comprises a solvent which is selected from toluene, dimethylformamide, and mixtures therof.

17. The process of claim 12 wherein the organic solvent comprises a solvent which is dimethylacetamide.

18. The process of claim 12 wherein the reaction is conducted at room temperature.

* * * * *